United States Patent [19]

Gauthier

[11] Patent Number: 4,838,254

[45] Date of Patent: Jun. 13, 1989

[54] SURGICAL FASTENING CLIP

[76] Inventor: Georges Gauthier, 85 Cours Albert Thomas, Lyon 3e, Rhone, France

[21] Appl. No.: 87,993

[22] Filed: Aug. 17, 1987

[30] Foreign Application Priority Data

Aug. 18, 1986 [FR] France ................................. 86 12052

[51] Int. Cl.$^4$ ................................................ A61F 5/04
[52] U.S. Cl. ............................ 128/92 YF; 128/92 YC
[58] Field of Search ............... 132/50 R, 68; 128/924, 128/924 F, 924 E, 924 C, 924 D, 334 R, 337; 24/150 B

[56] References Cited

U.S. PATENT DOCUMENTS

| | | | |
|---|---|---|---|
| 115,633 | 6/1971 | Newton | 132/50 R |
| 581,634 | 4/1987 | Veal | 24/150 B |
| 1,202,412 | 10/1916 | O'Donnell | 24/150 B |
| 1,252,862 | 1/1918 | Thompson | 24/150 B |
| 1,315,926 | 9/1919 | Gasper, Jr. | 132/50 R |
| 1,547,862 | 7/1925 | Davis | 411/474 |
| 1,554,527 | 9/1925 | Saalfrank | 24/150 B |
| 1,708,005 | 4/1929 | Wilson | 24/150 B |
| 2,168,076 | 8/1939 | Walenta | 24/150 B |
| 3,166,072 | 1/1965 | Sullivan, Jr. | 128/334 C |
| 3,586,002 | 6/1971 | Wood | 128/337 |
| 3,939,828 | 2/1976 | Mohr et al. | 128/924 C |
| 4,263,903 | 4/1981 | Griggs | 128/924 C |
| 4,454,875 | 6/1984 | Pratt et al. | 128/334 R X |
| 4,665,906 | 5/1987 | Jeruis | 128/924 P |

OTHER PUBLICATIONS

Orthopedic Catalog, Richards Mfg. Co., Memphis, TN, Nov. 15, 1974, p. 72.

Primary Examiner—Robert A. Hafer
Assistant Examiner—Kevin G. Rooney
Attorney, Agent, or Firm—Browdy and Neimark

[57] ABSTRACT

A fastening clip comprises two lateral rods, approximately parallel, connected together by a straight or curved central part, forming a bridge. The central part is curved and is placed so that the plane of its median axis forms an angle with a plane containing the median axes of the two parallel rods. The clip is particularly useful in osteosynthesis applications.

6 Claims, 3 Drawing Sheets

SURGICAL FASTENING CLIP

FIELD OF THE INVENTION

This invention has as its object a fastening clip, particularly for osteosynthesis, and a process for making the clip. The clip can be used particularly as a means for fastening in materials that are relatively not very resistant such as wood or its derivatives, plastic synthetic materials, or for bone fastening, called osteosynthesis.

BACKGROUND OF THE INVENTION

It is acknowledged that knitting of a fracture is impossible or almost impossible if there are movements of notable amplitude in the direction of the shear at the fracture surface. On the other hand, the knitting occurs in a manner that is all the more favorable if variable and not excessive pressure stresses are applied perpendicular to the fracture. Presently available methods of osteosynthesis are far from achieving an ideal bone fastening which prevents shears and favors variable, non excessive pressure stresses perpendicular to the fracture.

Very diagrammatically it is possible to contrast two groups of known means of bone fastening: rigid fastening means, or heavy osteosynthesis, and flexible fastening means, or light osteosynthesis. Fastening means can be called heavy osteosynthesis which consists of bulky equipment such as screwed plates or pinnings after boring These means provide completely rigid immobilizations of the fracture zone. This rigidity indeed prevents shearing of the fractured zone which knits in almost all cases, but this rigidity does not permit, or only slightly permits, variable pressures perpendicular to the fracture zone favorable to knitting, so that the latter often occurs with extended periods, even very extended periods, in relation to the optimal possibilities of bone knitting. Further, the use of these means requires more or less devitalizing the tissues, and especially the bone, which entails a number of risks, the most serious of which is the risk of extensive septic contamination, at times serious, and often difficult to heal. Further, the removal of the osteosynthesis equipment, of course, is necessary; it is generally done about eighteen months after placement, to avoid lasting modifications of the bone physiology induced by the greatness of the rigidity of the equipment, consisting of spongialization or extensive osteoporosis of the bone thus relieved of its physiological function.

Light osteosynthesis means comprise small pins and standard clips some of which comprise two approximately parallel lateral rods, connected together by a bridge-forming straight or angular central part, and whose median axis is located in the same plane as that of the median axes of the lateral rods. These known means of light osteosynthesis offer the advantage of allowing the manifestation, at the fracture focus, of compressions induced by contractions of the skeletal muscles of the limb. Unfortunately, by themselves, they do not always satisfactorily prevent the shear movements which are particularly unfavorable to knitting and, when they are used alone, they entail risks of pseudoarthrosis. When supplementary holding means are added to them, such as a plaster cast, this is done to the detriment of the comfort of the patient and, as a general rule, cannot constitute an ideal immobilization of the fracture zones in the shear direction.

SUMMARY OF THE INVENTION

The clip according to the present invention aims at allowing a decidedly more satisfactory fastening of the bone elements in contact, because the bone elements are closer to optimal knitting conditions while, by this simple osteosynthesis, any devitalization of the bone is avoided. Thanks to its design and to a placement suited to the type of osteosynthesis, this clip avoids any shear, while allowing variable compressions perpendicular to the fracture zone.

In this clip, which is of the type mentioned above comprising two parallel lateral rods connected by a central bridge-forming part, the central part forms a single curve, without reversal point, so that its median axis is contained in a plane, and it is placed so that this plane forms an angle with a plane containing the median axes of the two rods. This bending angle is advantageously greater than 90°.

According to a preferred embodiment of the invention, the lateral rods of this clip have a circular section and unequal lengths, which respectively facilitates making of holes to receive them and their introduction into the holes.

To facilitate guiding of the lateral rods and to reduce the risks of deforming them, when the clip is put in place, the distal part, or free end of the lateral rod, advantageously has a diameter slightly less than that of the rest of each rod and, preferably, this distal part is polished to facilitate its sliding in the hole previously drilled in the bone.

This clip is preferably made of a biocompatible material which exhibits a good elasticity and a good mechanical strength, such as, for example, a metal such as a titanium alloy such as TA6V of medical quality.

According to a simple mode of using the invention, the process of production of this clip consists in shaping a wire of the desired metal into a hairpin, with a central curved connecting part, then in bending this central part in the direction of the two lateral branches, at a large angle, preferably, greater than 90°, and according to a preset curved shape not comprising a sharp angle.

New possibilities using both the qualities of plasticity and elasticity of its constitutive material result from the shape of this clip.

This clip in the shape of a bent hairpin allows, on the proximal part joining the two branches, placing a support on the surface of the material to be fastened by its bent central part. The fact that the metal of the clip is moldable aids in an exact adaptation, and several practical applications can be envisaged. The fact that the metal exhibits an elasticity allows micromovements.

BRIEF DESCRIPTION OF THE DRAWINGS

In any case, the invention will be understood with the help of the following description, with reference to the accompanying diagrammatic drawings representing an embodiment of this clip and several examples of its used in osteosynthesis.

DETAILED DESCRIPTION OF THE INVENTION

Figure 1:
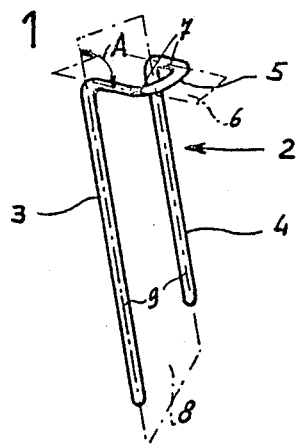
FIGS. 1 and 2 are views, respectively, in perspective and side elevation of the clip according to the invention.
Figure 2:
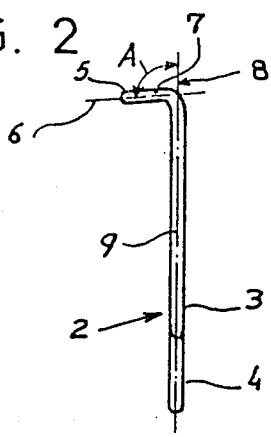

As shown is FIGS. 1 and 2, this clip 2 is of the type comprising two lateral rods 3 and 4, approximately parallel, connected together by a bridgeforming central part 5. According to the invention, the central part forming bridge 5 is curved and, further, it is placed so that plane 6, containing its median axis 7, forms with plane 8, containing median axes 9 of the two rods, a large angle A.

According to an advantageous embodiment of this clip 2, as illustrated in FIGS. 1 and 2, this angle A is slightly greater than 90°.

According to another advantageous characteristic of the invention, lateral rods 3 and 4 of this clip 2 are of circular section, which facilitates the making of drilled holes to receive them in the parts of the bone in whose holding they are to participate. Further, to facilitate their engagement in these holes, rods 3 and 4 are of unequal length. In the example illustrated in the drawing, rod 4 is longer than rod 3.

The holes in which lateral rods 3 and 4 of this clip should be engaged are drilled with the same diameter as the rods, so that their engagement in these holes, particularly if they are very long, can meet a resistance due to friction or binding forces. An accidental and undesirable deformation such as bending of one or both rods can result.

To remedy this, the distal part or free end of each lateral rod 3, 4 has a diameter slightly less than that of the rest of the rod. This finer end of each rod 3, 4 assures its role of guiding of the rod, under consideration, of the clip during its engagement in the hole drilled to receive it, without risk of binding.

To facilitate this engagement still more, each sharpened end of lateral rods 3, 4 of this clip is polished to slide better in its hole.

Of course, this clip 2 should be made of biocompatible material and exhibit both a good elasticity and a good mechanical strength. A metal like a titanium alloy such as TA6V of medical quality is perfectly suitable.

A very simple process for making this clip consists of shaping a wire of its constitutive material into a hairpin, with a curved bridge-forming central part 5, then bending this central part 5 in the direction of two lateral branches 3 and 4 at a large angle A, preferably, greater than 90°, this bending being performed to avoid deterioration of the mechanical qualities of the material. In particular, instrumentation is necessary which permits a regular curve and not a sharp angle, which is a factor for starting rupture. Further, as a function of the constitutive material, it is good to shape the clip under conditions which avoid cold-working or modifications of the mechanical qualities, for example, with heat.

Figure 3:
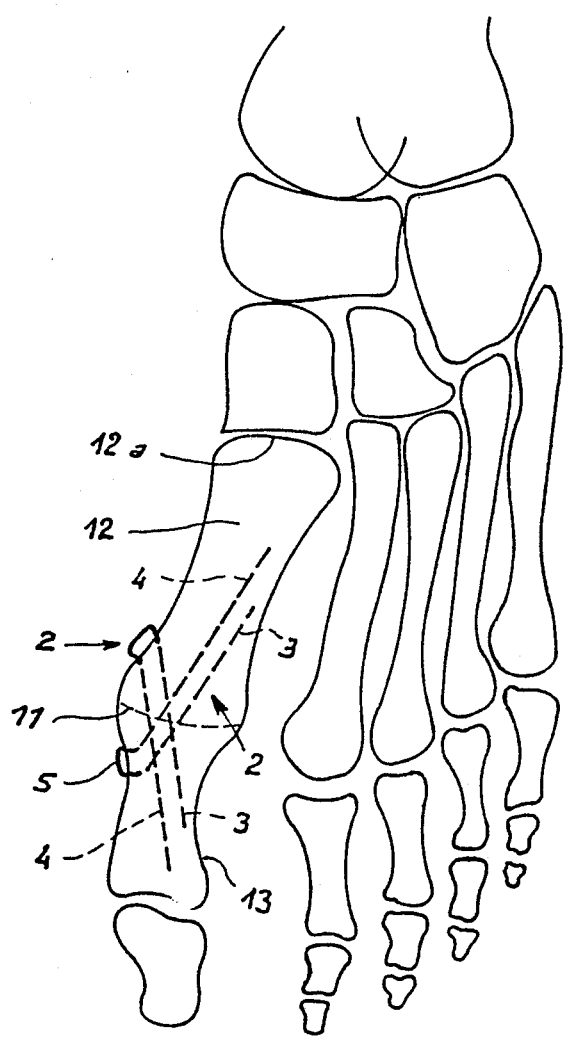
FIG. 3 is a top view of the skeleton of a left foot showing the application of this clip to an osteosynthesis for arthrodesis of the metatarsophalangeal joint of the big toe of this foot.

FIG. 3 illustrates the application of this clip to an osteosynthesis for arthrodesis of the metatarsophalangeal joint of the big toe of the left foot. In this application, each clip 2 is used in longitudinal osteosynthesis, i.e., their branches 3 and 4 are engaged in the bone in a direction close to that of the longitudinal axis of the bone considered, bridge-forming part 5 of each clip 2 being brought to cortical rest in the epiphysial bone.

It should be noted that arthrodesis of the first metatarsophalangeal joint, according to some statistics, exhibits a very high percentage of fastening failures when traditional fastening means, such as screws, are used. According to the invention, this fastening is achieved with at least one clip 2 whose two rods 3 and 4 are engaged approximately perpendicular to plane 11 of the bone union and therefore prevent any shear movement, both in translation and in rotation. If only a single clip 2 is used, its rods must be engaged on the inside of first metatarsal 12, to come close to its base 12a, curved central part 5 of this clip resting on the cortical of phalanx 13 of the big toe. This bent central part 5 allows, by percussion, a coaptation of fracture zone 11 to which fastening of rods 3 and 3 of clip 2 contributes which prevent its being pulled out. On the other hand, during muscular contractions, variable pressures favorable to the knitting can occur in this fracture zone.

As FIG. 3 shows, it is possible to use a second clip 2 whose rods 3 and 4 are engaged in the body of first phalanx 13 of the big toe.

Figure 4:
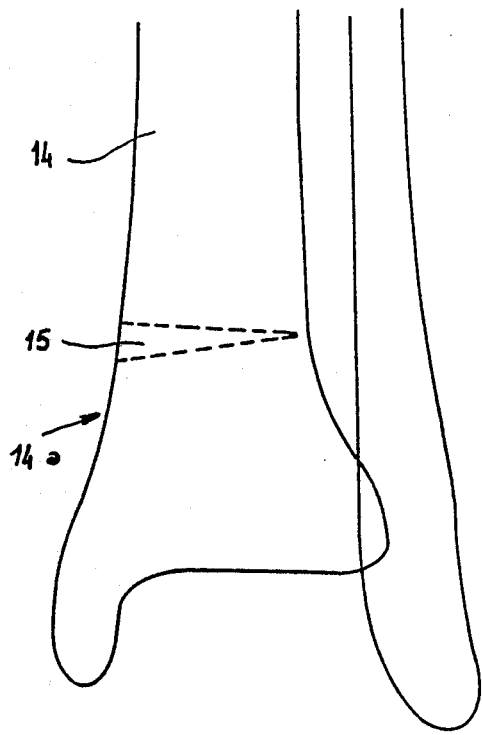
FIGS. 4 and 5 illustrate a mode of use of this clip for the correction of a deviation of a distal part of the tibia.
Figure 5:
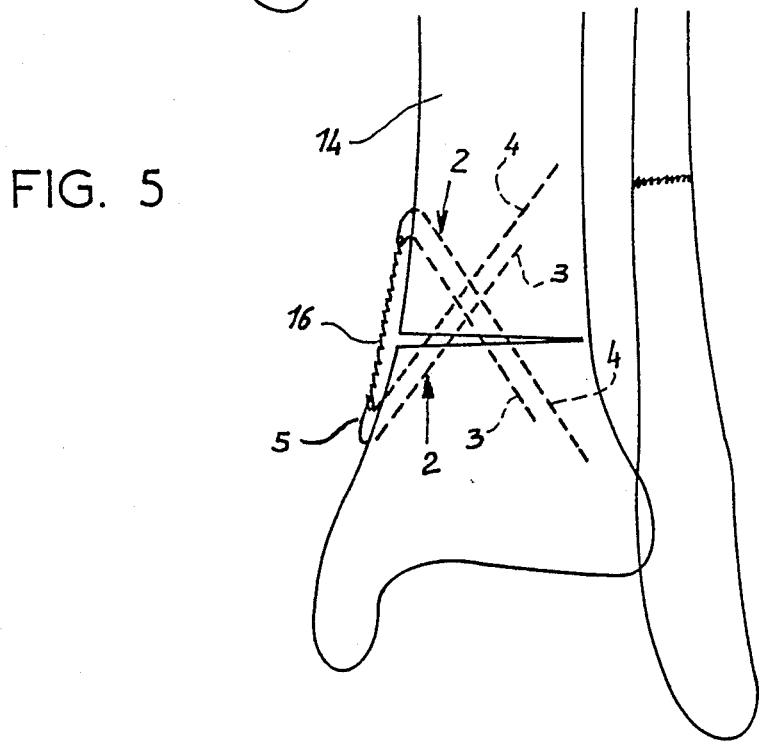

FIGS. 4 and 5 show another mode of use of this clip, in the case of its application to fastening of distal part 14a of tibia 14, after correction of a deviation of this tibia by resection of a part 15 in the shape of a wedge, which can be seen in FIG. 4. After resection of this part 15 of tibia 14, two clips 2 are implanted in tibia 14 so that each of them goes through the plane of section of both parts of this tibia to be coapted. As in the preceding application, two clips 2 prevent any displacement by rotation or by translation of the two surfaces in contact.

As shown in FIG. 5, in this application, coaptation of the surfaces in contact can be improved by using bent parts 5 of the two clips 2 as fastening head for a holding element or spring 16 which can be of metal of the same nature as clips 2, or of another biocompatible material and, particularly, of a biodegradable material such as polyglycol.

Figure 6:
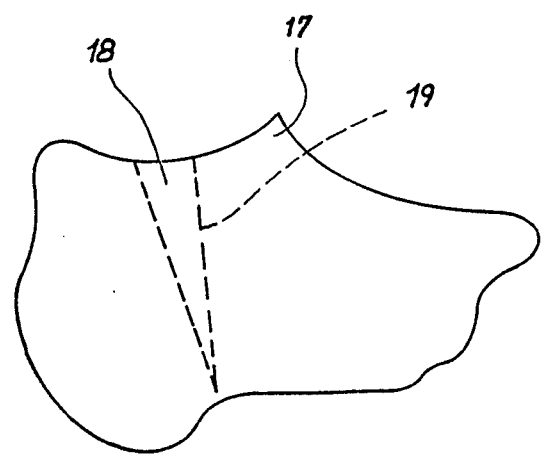
FIGS. 6 and 7 illustrate a third mode of use of this clip for the correction of a calcaneus.
Figure 7:
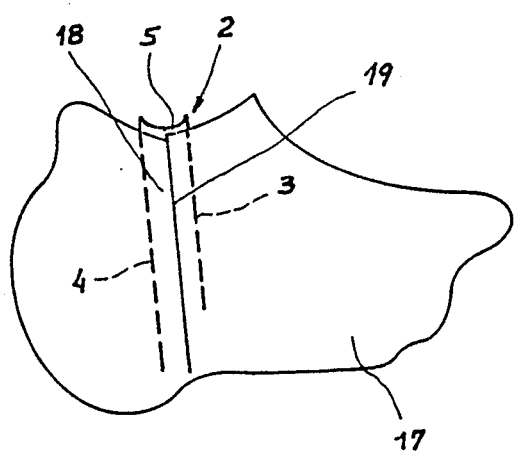

FIGS. 6 and 7 show another application of this clip 2 in which the coaptation of the two bone parts to be knitted is obtained by using the elasticity of bent part 5 of the clip. In the example illustrated by FIGS. 6 and 7, clip 2 is used as an elastic recall means of the two surfaces to be joined of a calcaneus 17 having first undergone a correction by resection. FIG. 6 shows this calcaneus 17 before correction by resection of a part 18 in the shape of a wedge.

As FIG. 7 shows, in this application, the elasticity of bent central part 5 of clip 2 is used to assure contact pressure of the two surfaces of fracture zone 19.

It was indicated above that clips 2 were advantageously made of titanium alloy TA6V of medical quality. Not only does this alloy exhibits a quite remarkable characteristic of absolute and constant biocompatibility but also it has qualities of mechanical strength very superior to the steels usually used in osteosynthesis, and more particularly it has excellent fatigue strength. Finally it exhibits the advantage of adhering easily to the bone and not causing any reaction of this latter by its contact.

However, it should be noted that its use is particularly difficult and that, to obtain its optimal qualities of mechanical strength, it must be worked at temperatures on the order of 950° C. to 1000° and under an argon atmosphere. It is easily understood that, under these conditions, machining of a complex part would entail considerable costs, considering, on the one hand, the cost of the material and, on the other hand, the complexity of its transformation technology. On the other hand, the simple shape of the clip according to the invention keeps its cost at a quite reasonable level.

It was indicated above that rods 3 and 4 of this clip 2 were advantageously of unequal length. Of course, it is also possible to make each clip 2 with rods 3 and 4 of the same length, the practitioner being able to cut the two branches to the desired lengths at the time of the operation.

It will be easily understood that, during this operation, the perforations made in the distal bone for engagement of rods 3 and 4 of each clip 2 are advantageously of a cross section slightly less than that of rods 3 and 4 of clip 2 considered to assure their good anchoring in this bone while the perforations made in the proximal bone are advantageously of a cross section equal to or slightly greater than that of rods 3 and 4, to favor their sliding.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A surgical fastening clip comprising:
   two lateral rods, each rod having a distal end and a median axis, said rods being of unequal lengths;
   a bridge-forming part connecting said two lateral rods in approximately parallel configuration;
   said bridge-forming part consisting of a single curve which curves in a single direction between its points of connection with said two rods so that a first plane containing the single curve forms a bending angle with a second plane containing the median axes of the two lateral rods, said bending angle being greater than 90° and said chip being formed of a biocompatible material having a good elasticity and a good mechanical strength.

2. The clip according to claim 1 wherein said lateral rods have a circular section.

3. The clip according to claim 1 wherein the distal end of each lateral rod has a diameter slightly less than the diameter of the remainder of the rod.

4. The clip according to claim 1 wherein the distal end of each lateral rod has a polished surface.

5. The clip according to claim 1 wherein the clip is constructed of a metal.

6. The clip of claim 5 wherein the clip is constructed of a titanium alloy.

* * * * *